(12) United States Patent
Genkin et al.

(10) Patent No.: US 10,406,150 B2
(45) Date of Patent: Sep. 10, 2019

(54) METHOD FOR TREATMENT OF PRIMARY HORMONE RESISTANT ENDOMETRIAL AND BREAST CANCERS

(71) Applicant: Lipoxen Technologies Limited, London (GB)

(72) Inventors: Dmitry Genkin, St. Petersburg (RU); Kirill Surkov, St. Petersburg (RU)

(73) Assignee: Lipoxen Technologies Limited, London (GB)

(*) Notice: Subject to any disclaimer, the term of this patent is extended or adjusted under 35 U.S.C. 154(b) by 0 days.

(21) Appl. No.: 15/476,617

(22) Filed: Mar. 31, 2017

(65) Prior Publication Data
US 2017/0202827 A1    Jul. 20, 2017

Related U.S. Application Data

(63) Continuation of application No. PCT/EP2015/075990, filed on Nov. 6, 2015.

(60) Provisional application No. 62/076,546, filed on Nov. 7, 2014.

(51) Int. Cl.
| | |
|---|---|
| *A61K 31/473* | (2006.01) |
| *A61K 31/135* | (2006.01) |
| *A61K 31/138* | (2006.01) |
| *A61K 31/40* | (2006.01) |
| *A61K 31/565* | (2006.01) |
| *A61K 31/57* | (2006.01) |
| *A61K 31/58* | (2006.01) |

(52) U.S. Cl.
CPC .......... *A61K 31/473* (2013.01); *A61K 31/135* (2013.01); *A61K 31/138* (2013.01); *A61K 31/40* (2013.01); *A61K 31/565* (2013.01); *A61K 31/57* (2013.01); *A61K 31/58* (2013.01)

(58) Field of Classification Search
None
See application file for complete search history.

(56) References Cited

FOREIGN PATENT DOCUMENTS

| | | | |
|---|---|---|---|
| RU | 2346691 C2 | | 2/2009 |
| WO | 2008/121028 | * | 10/2008 |
| WO | 2008/121029 | * | 10/2008 |
| WO | 2008121028 A2 | | 10/2008 |
| WO | 2008121029 A2 | | 10/2008 |

OTHER PUBLICATIONS

Carlson, "Past present, and future of hormonal therapy in recurrent endometrial cancer," Inter'l Journal of Women's Health, 201 4:6, pp. 429-435.
Progesterone, PubChem 2017.
Mometasone Furoate, PubChem 2017.
International Search Report, PCT/EP2015/075990, dated Mar. 2, 2016.
Hamilton, T.C., Characterization of a Human Ovarian Carcinoma Cell Line (NIH:OVCAR-3) with Androgen and Estrogen Receptors, Cancer research, vol. 43, 1983, p. 5379-5389.

* cited by examiner

*Primary Examiner* — Karl J Puttlitz
(74) *Attorney, Agent, or Firm* — Entralta P.C.; Peter D. Weinstein; James F. Fleming

(57) ABSTRACT

The invention provides a method for treatment of primary progesterone receptor-negative (PR−) endometrial cancer comprising administering (i) cridanimod or a salt or an ester thereof and (ii) a progesterone receptor (PR) agonist. The invention further provides a method for treatment of a primary estrogen receptor-negative (ER−) breast cancer, comprising administering (i) cridanimod or a salt or an ester thereof and (ii) a selective estrogen receptor modulator (SERM) or a selective estrogen receptor down-regulator (SERD). Also provided are compositions related to the above methods.

13 Claims, No Drawings

METHOD FOR TREATMENT OF PRIMARY HORMONE RESISTANT ENDOMETRIAL AND BREAST CANCERS

CROSS-REFERENCE TO RELATED APPLICATIONS

This application claims priority under 35 USC 111(a) to PCT/EP2015/075990, and also claims priority to U.S. Provisional Application No. 62/076,546, filed on Nov. 7, 2014, the disclosure of which are each herein incorporated by reference in its entirety.

FIELD OF THE INVENTION

The invention provides a method for treatment of primary progesterone receptor-negative (PR−) endometrial cancer comprising administering (i) cridanimod or a salt or an ester thereof and (ii) a progesterone receptor (PR) agonist. The invention further provides a method for treatment of a primary estrogen receptor-negative (ER−) breast cancer, comprising administering (i) cridanimod or a salt or an ester thereof and (ii) a selective estrogen receptor modulator (SERM) or a selective estrogen receptor down-regulator (SERD). Also provided are compositions related to the above methods.

BACKGROUND OF THE INVENTION

Endometrial cancer is one of the most common invasive gynecologic cancers. Currently no therapy of recurrent or metastatic endometrial carcinoma is available to patients.

Growth of the uterine endometrium is controlled by estrogen and progesterone. Endometrial carcinogenesis is related to estrogen overexposure that is not modulated by the differentiating effects of progesterone. The role of progesterone in the glandular epithelium of the endometrium is primarily to induce cellular differentiation and to antagonize estrogen-mediated cell proliferation. The biological functions of progesterone are mediated through progesterone receptors, which function as ligand-responsive transcription factors in the nucleus.

Expression of progesterone receptor (PR) has been positively correlated with response to progestin treatment and a good prognosis (Creasman et al., Obstet Gynecol 1980; 55:363-370). The overall response rate has been reported to be 72% in patients with progesterone receptor-rich tumors but only 12% in patients with progesterone receptor-poor lesions (Ehrlich et al., Am J Obstet Gynecol 1988; 158:796-807). Unfortunately, progestin treatment leads to depletion of PRs within the target tissue (Satyaswaroop et al., Cancer Lett 1992; 62:107-114). Thus, persistent expression of functional PR is likely to be required for successful progestin treatment.

The duration of efficacy for treatment with progestins is relatively short with progression-free intervals ranging from 2.5 to 8.5 months (Jacobsen et al., J Biol Chem. 2002; 277(31): 27793-27800). PR− cancers, especially primary PR− cancers, have previously been considered not treatable by hormone therapy. Some clinical guidelines recommend treatment of endometrial cancer (EC) with progestins, but only if it is PR+. See, e.g., M. M. Baekelandt 1 & M. Castiglione, Endometrial carcinoma: ESMO Clinical Recommendations for diagnosis, treatment and follow-up, Annals of Oncology 20 (Supplement 4): iv29-iv31, iv30 (2009) ("Progestational agents . . . are active in steroid receptor-positive tumors").

One of the main treatment modalities for non-operable breast cancer is hormonal therapy using antiestrogens. However, while such therapy is effective in 40-50% of breast cancer patients with tumors that are estrogen receptor-positive (ER+), it is effective only in 7-8% of patients with estrogen receptor-negative (ER−) disease (Parl et al., Cancer 1984; 54:2237-2242; Crowe et al., Surg Gynecol Obstet. 1991; 173:273-278; Aaltomaa et al., Ann Med. 1991; 23:643-648; Fisher et al., Lancet 2004; 364:858-868).

SUMMARY OF THE INVENTION

As specified in the Background Section, there is a great need in the art to develop novel methods for the treatment of endometrial and breast cancers, especially primary progesterone receptor-negative (PR−) endometrial cancer and primary estrogen receptor-negative (ER−) breast cancer. The present invention satisfies this and other needs by providing new methods and compositions for treatment of primary progesterone receptor-negative (PR−) endometrial cancer and primary estrogen receptor-negative (ER−) breast cancer.

In one aspect, the invention provides a method of treatment of a primary progesterone receptor-negative (PR−) endometrial cancer in a subject in need thereof, said method comprising administering to the subject (i) an effective amount of cridanimod or a salt or an ester thereof, wherein said effective amount is sufficient to sensitize cancer cells of the subject to inhibitory action of a progesterone receptor (PR) agonist, and (ii) a therapeutically effective amount of a PR agonist (collectively (i) and (ii) constituting a therapeutic treatment). In one embodiment, the above method of treatment results in complete response (CR) or partial response (CR/PR) or stable disease (SD) as per RECIST criteria (e.g., RECIST 1.0 or RECIST 1.1). In one embodiment, the PR agonist is progesterone. In another embodiment, the PR agonist is selected from the group consisting of medroxyprogesterone acetate, megestrol acetate, hydroxyprogesterone caproate, levonorgestrel, mometasone furoate, and synthetic progestin R5020. In one embodiment, the effective amount of cridanimod or salt or ester thereof is sufficient to induce PR in cancer cells of the subject. In one specific embodiment, the effective amount of cridanimod or salt or ester thereof induces PR in cancer cells of the subject to the level of more than 10 fmol PR receptors per mg of cytosol protein or until the equal or more than 1% of cancer cells become PR positive as determined by immunohistochemistry staining. In another embodiment, the effective amount of cridanimod or salt or ester thereof is sufficient to activate inactive form of PR in cancer cells of the subject. In one embodiment, the effective amount of cridanimod or salt or ester thereof is within the range of 1-50 mg/kg/day. In one embodiment, cridanimod or salt or ester thereof is administered in a single daily dose, or on each alternate day, or twice a week. In one embodiment, (i) cridanimod or salt or ester thereof and (ii) the PR agonist are administered concurrently (e.g., in one composition or in two separate compositions). In another embodiment, (i) cridanimod or salt or ester thereof is administered prior to (ii) the PR agonist. In one embodiment, prior to the administration of (i) cridanimod or salt or ester thereof and (ii) the PR agonist, the expression level of PRs is determined in a cancer sample obtained from the subject (e.g., using a ligand binding assay).

In a related aspect, the invention provides a pharmaceutical composition comprising (i) cridanimod or a salt or an ester thereof and (ii) a PR agonist. The invention also provides a method of treatment of a primary progesterone receptor-negative (PR−) endometrial cancer in a subject in need thereof, said method comprising administering to the subject a therapeutically effective amount of said pharmaceutical composition. In one embodiment, the pharmaceutical composition further comprises a pharmaceutically acceptable carrier or excipient. In one embodiment, the PR agonist is progesterone. In another embodiment, the PR agonist is selected from the group consisting of medroxyprogesterone acetate, megestrol acetate, hydroxyprogesterone caproate, levonorgestrel, mometasone furoate, and synthetic progestin R5020.

In a separate aspect, the invention provides a method of treatment of a primary estrogen receptor-negative (ER−) breast cancer in a subject in need thereof, comprising administering to the subject (i) an effective amount of cridanimod or a salt or an ester thereof, wherein said effective amount is sufficient to sensitize cancer cells of the subject to inhibitory action of a selective estrogen receptor modulator (SERM) or a selective estrogen receptor down-regulator (SERD), and (ii) a therapeutically effective amount of a SERM or a SERD (collectively (i) and (ii) constituting a therapeutic treatment). In one embodiment, the above method of treatment results in complete response (CR) or partial response (CR/PR) or stable disease (SD) as per RECIST criteria (e.g., RECIST 1.0 or RECIST 1.1). In one embodiment, the breast cancer is a triple-negative breast cancer. In one embodiment, the SERM is selected from the group consisting of tamoxifen, toremifen, lasofoxifene, droloxifene, iodoxifene, and EM 800. In one embodiment, the SERD is selected from the group consisting of fulvestrant, SR16234 (TAS108), ZK703, and ZK253. In one embodiment, the effective amount of cridanimod or salt or ester thereof is sufficient to induce estrogen receptor (ER) in cancer cells of the subject. In one specific embodiment, the effective amount of cridanimod or salt or ester thereof induces ER in cancer cells of the subject to the level of more than 10 fmol ER receptors per mg of cytosol protein or until the equal or more than 1% of cancer cells become ER positive as determined by immunohistochemistry staining. In one embodiment, the effective amount of cridanimod or salt or ester thereof is within the range of 1-50 mg/kg/day. In one embodiment, cridanimod or salt or ester thereof is administered in a single daily dose, or on each alternate day, or twice a week. In one embodiment, (i) cridanimod or salt or ester thereof and (ii) the SERM or SERD are administered concurrently (e.g., in one composition or in two separate compositions). In one embodiment, (i) cridanimod or salt or ester thereof is administered prior to (ii) the SERM or SERD. In one embodiment, prior to the administration of (i) cridanimod or salt or ester thereof and (ii) the SERM or SERD, the expression level of ERs is determined in a cancer sample obtained from the subject (e.g., using a ligand binding assay).

In a related aspect, the invention provides a pharmaceutical composition comprising (i) cridanimod or salt or ester thereof and (ii) a selective estrogen receptor modulator (SERM) or a selective estrogen receptor down-regulator (SERD). The invention also provides a method of treatment of a primary estrogen receptor-negative (ER−) breast cancer in a subject in need thereof, said method comprising administering to the subject a therapeutically effective amount of said pharmaceutical composition. In one embodiment, the pharmaceutical composition further comprises a pharmaceutically acceptable carrier or excipient. In one embodiment, the SERM is selected from the group consisting of tamoxifen, toremifen, and lasofoxifene, droloxifene, iodoxifene, and EM 800. In one embodiment, the SERD is selected from the group consisting of fulvestrant, SR16234 (TAS108), ZK703, and ZK253.

In one embodiment of any of the treatment methods of the invention, the method further comprises administering a radiation therapy and/or an additional chemotherapy to the subject.

In one embodiment of any of the treatment methods of the invention, the subject is human.

In one embodiment of any of the treatment methods or pharmaceutical compositions of the invention, the cridanimod salt is sodium cridanimod.

These and other aspects of the present invention will be apparent to those of ordinary skill in the art in the following description and claims.

DETAILED DESCRIPTION OF THE INVENTION

Definitions

The term "primary progesterone receptor-negative (PR−) cancer" as used herein refers to:
(i) a cancer which has not been exposed to a progesterone receptor (PR) agonist treatment and initially has less than 10 fmol of PR receptors per mg of cytosol protein (e.g., as determined using quantification with radiolabeled promegestone (e.g., R 5020) in frozen tissue sections; see, e.g., Pichon and Milgrom, Cancer Res 1977; 37:464-471; De Goeij et al., J Steroid Biochem 1988; 29(5):465-74), or
(ii) a cancer which has less than 1% of cancer cells which are PR-positive (PR+) as determined by immunohistochemistry staining (e.g., as described in 2010 ASCO/CAP ER and PgR Guideline Recommendations; Hammond et al., Arch Pathol Lab Med. 2010; 134:907-922; Fitzgibbons et al., Arch Pathol Lab Med. 2010; 134:930-935), or
(iii) a cancer characterized by the presence of non-functional PR receptors in the tumor tissue (Bonneterre, J et al., Gynecol Oncol. 2015 September; 138(3):663-7), or
(iv) a cancer which has not initially clinically responded to a progestin therapy considered adequate for its treatment (i.e., no complete or partial response or stable disease after the first course of therapy as per RECIST criteria, as defined below).

The term "secondary progesterone receptor-negative (PR−) cancer" refers to a cancer which was initially a PR-positive (PR+) cancer, but which became hormone resistant (acquired hormone resistance) after exposure to a PR agonist.

The term "primary estrogen receptor-negative (ER−) cancer" refers to
(i) a cancer which has not been exposed to an estrogen receptor (ER) modulator treatment and initially has less than 10 fmol of ER receptors per mg of cytosol protein (e.g., determined as described in Pichon and Milgrom, Cancer Res 1977; 37:464-471; De Goeij et al., J Steroid Biochem 1988; 29(5):465-74), or
(ii) a cancer which has less than 1% of cancer cells which are ER-positive (ER+) as determined by immunohistochemistry staining (e.g., as described in 2010 ASCO/CAP ER and PgR Guideline Recommendations; Hammond et al., Arch Pathol Lab Med. 2010; 134:907-922; Fitzgibbons et al., Arch Pathol Lab Med. 2010; 134:930-935), or
(iii) a cancer which has not initially clinically responded to a hormonal (e.g., anti-estrogen or aromatase inhibitor) therapy considered adequate for its treatment (i.e., no complete or partial response or stable disease after the first course of therapy as per RECIST criteria, as defined below).

The term "secondary estrogen receptor-negative (ER−) cancer" refers to a cancer which was initially a ER+ cancer, but which became hormone resistant (acquired hormone resistance) after exposure to an ER modulator.

The term "triple-negative breast cancer" refers to a cancer wherein cancer cells do not express estrogen receptor (ER), progesterone receptor (PR), and HER2 protein. HER2 negativity can be determined, e.g., by the IHC (Immunohistochemistry) method and/or ISH (in situ hybridization) method (see, e.g., 2013 ASCO-CAP HER2 Test Guideline Recommendations; Wolff, J Clin Oncol. 2013; 31(31):3997-4013) if a single test IHC or ISH, correspondingly (or both tests) show (i) IHC 1+ as defined by incomplete membrane staining that is faint/barely perceptible and within >10% of the invasive tumor cells; (ii) IHC 0 as defined by no staining observed or membrane staining that is incomplete and is faint/barely perceptible and within ≤10% of the invasive tumor cells; (iii) ISH negative based on single-probe average HER2 copy number <4.0 signals/cell; (iv) dual-probe HER2/CEP17 ratio <2.0 with an average HER2 copy number <4.0 signals/cell.

The term "progesterone receptor (PR) agonist" means an agent that binds to and activates progesterone receptors.

The term "selective estrogen receptor modulator" or "SERM" means an agent that activates some estrogen receptors but not others, thereby having estrogen-like effects on target tissues with no effect or anti-estrogen effect on other tissues that have estrogen receptors: their action is different in various tissues, thereby granting the possibility to selectively inhibit or stimulate estrogen-like action in various tissues.

The term "selective estrogen receptor down-regulator" or "SERD" means an agent that competitively binds to estrogen receptors and makes the receptors unavailable or unresponsive to estrogen or estrogen agonists (such agent is also called "pure antagonist").

The terms "RESICT" or "Response Evaluation Criteria In Solid Tumors" refer to a set of published rules that define when cancer patients improve ("respond"), stay the same ("stable") or worsen ("progression") during treatments. The original criteria RECIST 1.0 were published in February 2000 by an international collaboration including the European Organization for Research and Treatment of Cancer (EORTC), National Cancer Institute (NCI) of the United States and the National Cancer Institute of Canada Clinical Trials Group (Therasse et al., J. Natl. Cancer Inst., 2000, 92(3):205-216). RECIST 1.1, published in January 2009 (Eisenhauer et al., Eur. J. Cancer, 2009, 45:228-247), is an update to the original criteria. Currently, the majority of clinical trials evaluating cancer treatments for objective response in solid tumors are using RECIST.

As used herein the term "therapeutically effective" applied to dose or amount refers to that quantity of a compound or pharmaceutical composition that is sufficient to result in a desired activity upon administration to a subject in need thereof. Within the context of the present invention, when the term "therapeutically effective" is used (e.g., in connection with an amount of PR agonist or a SERM or a SERD), it refers to that quantity of the compound or a pharmaceutical composition containing such compound that is sufficient to delay the manifestation, arrest the progression, relieve or alleviate at least one symptom of a cancer treated by the methods of the present invention. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (MJ. Gait ed. 1984); Nucleic Acid Hybridization (B. D. Hames & S. J. Higgins eds. (1985>>>; *Transcription and Translation* (B. D. Hames & S. J. Higgins, eds. (1984>>; *Animal Cell Culture* (R. I. Freshney, ed. (1986>>>; *Immobilized Cells and Enzymes* (IRL Press, (1986>>>; B. Perbal, *A practical Guide To Molecular Cloning* (1984); F. M. Ausubel et al. (eds.), *Current Protocols in Molecular Biology*, John Wiley & Sons, Inc. (1994); among others.

Methods of the Invention

In one embodiment, the invention provides a method of treatment of a primary progesterone receptor-negative (PR−) endometrial cancer in a subject in need thereof, said method comprising administering to the subject (i) an effective amount of cridanimod or a salt or an ester thereof, wherein said effective amount is sufficient to sensitize cancer cells of the subject to inhibitory action of a progesterone receptor (PR) agonist, and (ii) a therapeutically effective amount of a PR agonist.

In a separate embodiment, the invention provides a method of treatment of a primary estrogen receptor-negative (ER−) breast cancer in a subject in need thereof, comprising administering to the subject (i) an effective amount of cridanimod or a salt or an ester thereof, wherein said effective amount is sufficient to sensitize cancer cells of the subject to inhibitory action of a selective estrogen receptor modulator (SERM) or a selective estrogen receptor down-regulator (SERD), and (ii) a therapeutically effective amount of a selective ER modulator or SERD. In a specific embodiment, the primary ER− breast cancer is a triple-negative breast cancer.

In the above methods of the invention, cridanimod or salt or ester thereof can be administered in a single daily dose, or on each alternate day, or twice a week. The daily dose can vary from 0.5 to 1000 mg/kg/day, preferably from 1 to 200 mg/kg/day, most preferably from 1 to 50 mg/kg/day (calculated based on 9-oxoacridine-10-acetic acid). Specific daily dosages will normally be determined by the prescribing physician with the dosage generally varying according to the age, weight, and response of the individual patient, as well as the severity of the patient's symptoms.

In the methods of the invention, a PR agonist or a SERM or a SERD can be administered according to therapeutic protocols well known in the art. It will be apparent to those skilled in the art that the administration of these agents can be varied depending on the disease being treated, parameters of an individual patient, and the observed responses.

In a specific embodiment of each of the above methods, the method involves determining the expression level of PRs or ERs in a cancer sample obtained from the subject in order to verify the primary PR− or primary ER− cancer status.

Suitable cancer samples can be, e.g., biopsy samples, including without limitation fresh tissue samples, formalin fixed, paraffin-embedded (FFPE) and frozen samples. Various methods for determining the expression level of PRs or ERs include mRNA-based and protein-based methods. Non-limiting examples of mRNA-based methods include, e.g., polymerase chain reaction (PCR) based methods (e.g., quantitative real time PCR (qRT-PCR)), microarray analysis, fluorescent in situ hybridization (FISH) assays, Northern blotting, and new generation sequencing methods. Non-limiting examples of protein-based methods include, e.g., quantification with radiolabeled ligand (e.g., as described in Pichon and Milgrom, Cancer Res 1977; 37:464-471; De Goeij et al., J Steroid Biochem 1988; 29(5):465-74) or immunodetection (e.g. immunoblotting, enzyme-linked immunosorbant assay (ELISA), immunohistochemistry staining (e.g., as described in Fitzgibbons et al., Arch Pathol Lab Med. 2010; 134:930-935)). Antibodies recognizing PR or ER, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

Therapeutic methods of the invention can be combined with additional anti-cancer therapies such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include antiangiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, VEGF antagonists, VEGF receptor antagonists (such as anti-VEGF antibodies), VEGF variants, soluble VEGF receptor fragments, aptamers capable of blocking VEGF or VEGFR, neutralizing anti-VEGFR antibodies, inhibitors of VEGFR tyrosine kinases, and any combinations thereof (e.g., anti-hVEGF antibody A4.6.1, bevacizumab or ranibizumab). See also Carmeliet and Jain (2000).

Non-limiting examples of chemotherapeutic compounds which can be used in combination treatments of the present invention include, for example, aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estramnustine, etoposide, exemestane, filgrastim, fludarabine, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, temozolomide, teniposide, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan); growth factor signal transduction kinase inhibitors; mitochondrial dysfunction inducers; and chromatin disruptors.

Pharmaceutical Compositions of the Invention and Administration

In conjunction with the above methods, the invention provides a pharmaceutical composition comprising (i) cridanimod or a salt or an ester thereof and (ii) a progesterone receptor (PR) agonist. In a separate embodiment, the invention provides a pharmaceutical composition comprising (i) cridanimod or a salt or an ester thereof and (ii) a selective estrogen receptor modulator (SERM) or a selective estrogen receptor down-regulator (SERD).

Also provided herein are pharmaceutical compositions containing a single active ingredient (i.e., cridanimod or a salt or an ester thereof, a PR agonist, or a SERM or a SERD), wherein two or more compositions (one being cridanimod or a salt or an ester thereof) are co-administered in the methods of the invention.

Cridanimod (also known as 9-oxoacridine-10-acetic acid, (9-oxoacridine 10(9H)-yl)acetic acid, 9-oxo-10(9H)acridineacetic acid, 2-(9-oxoacridin-10-yl) acetic acid, and 10-(carboxymethyl)-9(10H)acridone (CMA); CAS 38609-97-1; see also U.S. Pat. No. 3,681,360) has the following structure:

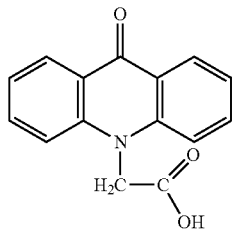 [SMILES: O=C(O)Cn1c2ccccc2c(=O)c2ccccc21]

It shall be appreciated that, as used in the present application, when cridanimod is mentioned, its pharmaceutically acceptable salts and esters are also meant, if not specified otherwise.

Numerous pharmaceutical compositions containing cridanimod salts are known. Non-limiting examples include cridanimod sodium salt (preparation Neovir, Register of Drugs of Russia, Drugs Encyclopedia, RDR-11th issue, Chief-Redactor Vishkovskiy A. L., Moscow, RDR-2004, 1503), mixtures of 9-oxoacridine-10-acetic acid and salt-forming agent/solubilizer, for example, methylaminoalcohol (preparation Cycloferon containing 1-deoxy-1-(methylamino)-D-glucitol (Meglumine) as a solubilizer, Register of Drugs of Russia, Drugs Encyclopedia, RDR-11th issue, Chief-Redactor Vishkovskiy A. L., Moscow, RDR-2004, 1503 pp.) or N, N-dimethylaminoisopropylglucose, namely 3-O—(N,N-dimethylamino-n-propyl-1,2:5,6-di-O-isopropyliden-α-, D-glucofuranose (preparation Anandin, patent RU 2197248).

TABLE 1

Composition of Virexxa and Neovir®

| Composition of Virexxa | Amount per ml | Composition of Neovir® | Function |
| --- | --- | --- | --- |
| Sodium Cridanimod | 125.0 mg | Sodium Cridanimod | Active |
| Sodium Citrate | 2.5 mg | Sodium Citrate | Buffer component |
| Citric Acid Monohydrate | q.s to 0.25 mg | Citric Acid Monohydrate | Buffer component for adjustment of pH value (7.5-8.3) |
| Water for injection | ad 1.0 ml | Water for injection | Solvent |

The pharmaceutically acceptable salts derived from the salt forming bases could be obtained with inorganic or organic bases. The salts with inorganic bases include, but are not limited to, sodium, potassium, lithium, ammonium, calcium and magnesium salts. The salts with organic bases include, but are not limited to, salts of primary, secondary, tertiary and quaternary amines, such as alkylamines, dialkylamines, trialkylamines, substituted alkylamines, di(substituted alkyl)amines, tri(substituted alkyl)amines, alkenylamines, dialkenylamines, trialkenylamines, substituted alkenylamines, di(substituted alkenyl)amines, tri(substituted alkenyl)amines, cycloalkylamines, di(cycloalkyl)amines tri(cycloalkyl)amines, substituted cycloalkylamines, di(substituted cycloalkyl)amines, tri(substituted cycloalkyl)amines, cycloalkenylamines, di(substituted cycloalkenyl)amines, di(substituted cycloalkenyl)amines, arylamines, diarylamines, triarylamines, heteroarylamines, diheteroarylamines, triheteroarylamines, heterocyclylamines, diheterocyclylamines, triheterocyclylamines, mixed di- and tri-amines, where at least one of the substitutes on amine differs and is selected from the group, including alkyl, substituted alkyl, alkenyl, substituted alkenyl, aryl, heteroaryl, heterocyclyl, etc. Amines, in which two or three substitutes together with the nitrogen atom to which they are connected, form a heterocyclyl or a heteroaryl, also are included here. Non-limiting examples of appropriate amines include, in particular, isopropylamine, trimethylamine, diethylamine, tri(isopropyl)amin, tri(<<-propyl)amine, ethanolamine, 2-dimethylaminoethanol, tromethamine, lysine, arginine, histidine, caffeine, procaine, choline, betaine, ethylendiamine, glucosamine, N-alkylglucamine, theobromine, purines, piperazine, piperidine, morpholine, N-ethylpiperidine etc. Non-limiting examples of appropriate cations are, in particular, cations of 3-O—(N,N-dimethylamino-n-propyl)-1,2:5,6-di-O-isopropyliden-α,D-glucofuranose, 1-deoxy-1-(ethylamino)-D-glucitol (i.e. eglumine), 1-deoxy-1-(propylamino)-D-glucitol, 1-deoxy-1-(butylamino)-D-glucitol, 1-deoxy-1-(methylamino)-L-glucitol, 1-deoxy-1-(ethylamino)-L-glucitol, 1-deoxy-1-(propylamino)-L-glucitol, and 1-deoxy-1-(butylaniino)-L-glucitol.

Esters of cridanimod include, but are not limited to, compounds obtained by hydrogen atom substitution in acid OH-group with an organic group R. Non-limiting examples of suitable esters include but are not limited to, esters of 9-oxoacridine-10-acetic acid with lower alkyls (namely with (CrC 12)alkyls, in particular ethyl, propyl, isopropyl, butyl and amyl esters), as well as with choline and other lypophilic alcohols. After rapid penetration through biological membranes in vivo, these compounds are easily hydrolyzed to free 9-oxoacridine-10-acetic acid.

Non-limiting examples of PR agonists which can be used in the compositions of the present invention include, e.g., medroxyprogesterone acetate, megestrol acetate, hydroxyprogesterone caproate, levonorgestrel, mometasone furoate, synthetic progestin R5020, and progesterone. Non-limiting examples of SERMs which can be used in the compositions of the present invention include, e.g., tamoxifen, toremifen, lasofoxifene, droloxifene, iodoxifene, and EM 800 (Tremblay et al., Endocrinology, 1998, 139:111-118). Non-limiting examples of SERDs which can be used in the compositions of the present invention include, e.g., fulvestrant (Faslodex) (Wakeling et al., Cancer Res., 1991, 51:3867-3873; Howell et al., Cancer, 2000, 89:817-825), SR16234 (TAS108) (Buzdar, Clinical Cancer Research, Jan. 15, 2005 (Suppl.) 11:906s-908s), ZK703 (Hoffmann et al., J. Natl. Cancer Inst., 2004, 96(3): 210-218), and ZK253 (Hoffmann et al., J. Natl. Cancer Inst., 2004, 96(3): 210-218).

In the pharmaceutical compositions of the invention active ingredient(s) (cridanimod or a salt or an ester thereof, a PR agonist, or a SERM, or a SERD) may be combined with pharmaceutically acceptable carriers, excipients or diluents, according to standard pharmaceutical practice.

The pharmaceutical compositions of the invention can be administered orally or parenterally, including the intravenous, intra-muscular, intraperitoneal, subcutaneous, rectal and topical routes of administration. The pharmaceutical compositions of the invention can be administered locally to the area in need of treatment. This may be achieved by, for example, but not limited to, local infusion during surgery, injection, catheter, or implant. Said implant can be made, e.g., out of a porous, non-porous, or gelatinous material, including membranes, such as sialastic membranes or fibers. The administration can also be by direct injection at the site (or former site) of a tumor or neoplastic or pre-neoplastic tissue.

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, or cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil. Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol.

Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation. The injectable solutions or microemulsions may be introduced into a patient's blood-stream by local bolus injection.

Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions used in the methods of the instant invention may also be in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., can be used. As used herein, topical application can include mouth washes and gargles.

When used as different pharmaceutical compositions, (i) cridanimod or a salt or an ester thereof and (ii) a PR agonistor, or a SERM, or a SERD ("second agent") can be administered by different routes. For example, cridanimod or a salt or an ester thereof may be administered orally to generate and maintain good blood levels thereof, while the second agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of the second agent will depend upon the diagnosis of the attending physicians and their judgment of the condition of the patient and the appropriate treatment protocol.

Cridanimod or a salt or an ester thereof, and chemotherapeutic agent and/or radiation may be administered concurrently (simultaneously or essentially simultaneously, in one, two or more compositions) or sequentially.

For monitoring treatment efficiency, size of the tumor (or metastasis) can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In other aspects of this embodiment, a therapeutic treatment disclosed herein reduces the size of an endometrial and/or breast cancer tumor by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic treatment disclosed herein reduces the size of an endometrial and/or breast cancer tumor from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein may comprise a therapeutic treatment in an amount sufficient to allow customary administration to an individual. In aspects of this embodiment, a pharmaceutical composition disclosed herein may be, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic treatment. In other aspects of this embodiment, a pharmaceutical composition disclosed herein may be, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic treatment. In yet other aspects of this embodiment, a pharmaceutical composition disclosed herein may be in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may be in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic treatment disclosed herein. In other aspects of this embodiment, a pharmaceutical composition disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic treatment disclosed herein in a pharmaceutical composition disclosed herein may be of any concentration desired. In an aspect of this embodiment, the final concentration of a therapeutic treatment in a pharmaceutical composition may be a therapeutically effective amount. In other aspects of this embodiment, the final concentration of a therapeutic treatment in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic treatment disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic treatment in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, treating an individual suffering from endometrial and/or breast cancer. As used herein, the terms "treating", "treat", "treatment", and the like refer to reducing or eliminating in an individual a clinical symptom of endometrial and/or breast cancer; or delaying or preventing in an individual the onset of a clinical symptom of endometrial and/or breast cancer; or slowing or reversing the progression of endometrial and/or breast cancer. For example, the term "treating" can mean reducing a symptom of endometrial and/or breast cancer, including, but not limited to, reducing tumor size, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%, or eliminating or reducing a patient's tumor burden, or preventing, delaying or inhibiting metastasis. As another example, the term "treating" can mean controlling a symptom of endometrial and/or breast cancer such as, e.g., reducing the number of symptoms per given time period and/or the severity of a symptom. The actual symptoms associated with endometrial and/or breast cancer are well known and can be determined by a person of ordinary skill in the art by taking into account factors, including, without limitation, the location of the cancer, the cause of the endometrial and/or breast cancer, the severity of the endometrial and/or breast cancer, and/or the cells, tissue or organ affected by the endometrial and/or breast cancer. Those of skill in the art will know the appropriate symptoms or indicators associated with a specific type of endometrial and/or breast cancer and will know how to determine if an individual is a candidate for treatment as disclosed herein.

In aspects of this embodiment, a therapeutically effective amount of a therapeutic treatment disclosed herein reduces a symptom associated with endometrial and/or breast cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic treatment disclosed herein reduces a symptom associated with endometrial and/or breast cancer by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic treatment disclosed herein reduces a symptom associated with endometrial and/or breast cancer by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic treatment disclosed herein generally is in the range of about 0.001 mg/kg/day to about 100 mg/kg/day. In aspects of this embodiment, an effective amount of a therapeutic treatment disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic treatment disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic treatment disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic treatment disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic treatment disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic treatment disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of an endometrial and/or breast cancer therapeutic disclosed herein typically may be between about 50 mg/mL to about 1,000 mg/mL. In aspects of this embodiment, a therapeutically effective amount of an endometrial and/or breast cancer therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

Dosing can be single dosage or cumulative (serial dosing), and can be readily determined by one skilled in the art. For instance, treatment of an endometrial and/or breast cancer may comprise a one-time administration of an effective dose of a pharmaceutical composition disclosed herein. Alternatively, treatment of an endometrial and/or breast cancer may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In aspects of this embodiment, a therapeutic treatment disclosed herein reduces the frequency of a symptom of an endometrial and/or breast cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In other aspects of this embodiment, a therapeutic treatment disclosed herein reduces the frequency of a symptom of an endometrial and/or breast cancer over a given time period by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In one embodiment, an endometrial and/or breast cancer therapeutic disclosed herein is capable of reducing the number of cancer cells or tumor size in an individual suffering from endometrial and/or breast cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, an endometrial and/or breast cancer therapeutic is capable of reducing the number of cancer cells or tumor size in an individual suffering from endometrial and/or breast cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

A drug delivery platform includes both a sustained release drug delivery platform and an extended release drug delivery platform. As used herein, the term "sustained release" refers to the release of a therapeutic treatment disclosed herein over a period of about seven days or more. As used herein, the term "extended release" refers to the release of a therapeutic treatment disclosed herein over a period of time of less than about seven days.

In aspects of this embodiment, a sustained release drug delivery platform releases a therapeutic treatment disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic treatment disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release drug delivery platform releases a therapeutic treatment disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release drug delivery platform releases a therapeutic treatment disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a drug delivery platform releases a therapeutic treatment disclosed herein with substantially zero order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic treatment disclosed herein with substantially zero order release kinetics over a period of, e.g., at most 1 day after administration, at most 2 days after administration, at most 3 days after administration, at most 4 days after administration, at most 5 days after administration, or at most 6 days after administration.

In aspects of this embodiment, a drug delivery platform releases a therapeutic treatment disclosed herein with substantially first order release kinetics over a period of, e.g., about 1 day after administration, about 2 days after administration, about 3 days after administration, about 4 days after administration, about 5 days after administration, or about 6 days after administration. In other aspects of this embodiment, a drug delivery platform releases a therapeutic treatment disclosed herein with substantially first order release kinetics over a period of, e.g., at most 1 day after administration, at most 2 days after administration, at most 3 days after administration, at most 4 days after administration, at most 5 days after administration, or at most 6 days after administration.

In a further embodiment, an endometrial and/or breast cancer therapeutic and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of an endometrial and/or breast cancer therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of an endometrial and/or breast cancer therapeutic disclosed herein reduces a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of an endometrial and/or breast cancer therapeutic disclosed herein reduces a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of an endometrial and/or breast cancer therapeutic disclosed herein reduces a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A pharmaceutical composition or endometrial and/or breast cancer therapeutic is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with some form of endometrial and/or breast cancer. Pre-operative evaluation typically includes routine history and physical examination in addition to thorough informed consent disclosing all relevant risks and benefits of the procedure.

A therapeutic treatment disclosed herein, or a composition comprising such a therapeutic treatment, may be made into a solid formulation. Solid formulations suitable for enteral or parenteral administration include, without limitation, capsules, tablets, pills, troches, lozenges, powders and granules suitable for inhalation or for reconstitution into sterile injectable solutions or dispersions. A therapeutic treatment or composition disclosed herein intended for such administration may be prepared according to any method known to the art for the manufacture of pharmaceutical compositions. In such solid dosage forms, the therapeutic treatment may be admixed with (a) at least one inert customary excipient (or carrier), such as, e.g., sodium citrate or dicalcium phosphate or (b) fillers or extenders, as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium treatments, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. In solid formulations, a therapeutically effective amount of a therapeutic treatment disclosed herein typically may be between about 0.0001% (w/w) to about 60% (w/w), about 0.001% (w/w) to about 40.0% (w/w), or about 0.01% (w/w) to about 20.0% (w/w).

A therapeutic treatment disclosed herein, or a composition comprising such a therapeutic treatment, may be made into a semi-solid formulation. Semi-solid formulations include, without limitation, ointments, creams, salves, and gels. A therapeutic treatment or composition disclosed herein intended for such administration may be prepared according to any method known to the art for the manufacture of pharmaceutical compositions. In semi-solid formulations, a therapeutically effective amount of a therapeutic treatment disclosed herein typically may be between about 0.0001% (w/v) to about 60% (w/v), about 0.001% (w/v) to about 40.0% (w/v), or about 0.01% (w/v) to about 20.0% (w/v). In semi-solid formulations, a therapeutically effective amount of a therapeutic treatment disclosed herein typically may also be between about 0.0001% (w/w) to about 60% (w/w), about 0.001% (w/w) to about 40.0% (w/w), or about 0.01% (w/w) to about 20.0% (w/w).

A therapeutic treatment disclosed herein, or a composition comprising such a therapeutic treatment, may be made into a liquid formulation. Liquid formulations suitable for enteral or parenteral administration include, without limitation, solutions, syrups, elixirs, dispersions, emulsions, and suspensions. A therapeutic treatment or composition disclosed herein intended for such administration may be prepared according to any method known to the art for the manufacture of pharmaceutical compositions. In such liquid dosage forms, a therapeutic treatment or composition disclosed herein may be admixed with (a) suitable aqueous and nonaqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size. In liquid formulations, a therapeutically effective amount of a therapeutic treatment disclosed herein typically may be between about 0.0001% (w/v) to about 60% (w/v), about 0.001% (w/v) to about 40.0% (w/v), or about 0.01% (w/v) to about 20.0% (w/v).

Syrups and elixirs may be formulated with sweetening agents, for example glycerol, propylene glycol, sorbitol or sucrose. Such formulations may also contain a demulcent, a preservative, flavoring agents, and coloring agents.

Liquid suspensions may be formulated by suspending a therapeutic treatment disclosed herein in admixture with excipients suitable for the manufacture of aqueous suspensions. Such excipients are suspending agents, for example sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids, for example polyoxyethylene sorbitan monooleate.

In an embodiment, in instances in which each of the therapeutics themselves are administered, without limitation, as individual or separate dosage forms (e.g., capsules or tablets), the kit comprises, without limitation, each of the therapeutics making up the composition of the invention, along with instructions for use. In an additional embodiment, the therapeutic components, without limitation, may be packaged in any manner suitable for administration, so long as the packaging, when considered along with the instructions for administration, without limitation, clearly indicates the manner in which each of the therapeutic components is to be administered. In a further embodiment, each of the therapeutics or a combination of such therapeutics may, without limitation, be combined into a single administrable dosage form such as a capsule, tablet, or other solid or liquid formulation. The therapeutic can be provided to an individual in a package. The package can be a container, for instance, without limitation, a bottle, a canister, a tube or other enclosed vessel. The package can also be a packet, such as a blister pack. In an embodiment, the individual or separate dosage is in the form of a blister pack. In an aspect of this embodiment, a blister pack is a term for several types of pre-formed plastic packaging used for small consumer goods, foods, and for pharmaceuticals. In a further embodiment, a blister pack is comprised of a cavity or pocket made from a formable web, usually a thermoformed plastic and typically includes a backing of paperboard or a lidding seal of aluminum foil or plastic. In a further embodiment, a blister that folds onto itself is a clamshell. In an aspect of this embodiment, a blister pack is commonly used as unit-dose packaging for pharmaceutical tablets, capsules or lozenges. In an embodiment, a blister pack can provide barrier protection for shelf life requirements, and a degree of tamper resistance and can be used for packing physician samples of cancer therapeutic products.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Until the present invention, cridanimod has not been used in primary receptor negative endometrial or breast cancer patients, because hormonal therapy is contraindicated and considered unethical in this specific subset of patients (NCCN Clinical Practice Guidelines in Oncology, Uterine Neoplasms, Version 1.2014, NCCN.org and Endometrial Cancer: ESMO Clinical Practice Guidelines, Ann Oncol 2013; 24 (Suppl 6)).

Methods

Estrogen receptor (ER) and progesterone receptor (PR) in the cell suspension and tissues were assayed in cytosol using the radioligand binding assay (LBA) EORTC (year 1980) reference method (Revision of the standards for the assessment of hormone receptors in human breast cancer; report of the second E.O.R.T.C. Workshop, held on 16-17 Mar. 1979, in the Netherlands Cancer Institute. Eur J Cancer 16: 1513-1515). Results were expressed as fmol per mg cytosol protein. The cut-off for the classification of positive receptor status was 10 fmol/mg Immunohistochemistry staining (IHC) assay for ER and PR receptor status was performed using Dako ER/PR pharmDx kit (ER/PR pharm DX kit, Dako Corporation C; CA: 2008). Tumors with less than 1% of cancer cells which are ER positive (ER+) as determined by immunohistochemistry staining were considered "estrogen receptor-negative (ER−)". Tumors with less than 1% of cancer cells which are PR positive (PR+) as determined by immunohistochemistry staining were considered "progesterone receptor-negative (PR−)".

Example 1. A Combination of PR-Agonist and Sodium Cridanimod has Limited Efficacy in Secondary PR-Negative Endometrial Cancer with Acquired Resistance to PR-Agonist but is Highly Effective in Primary PR-Negative Endometrial Cancer Eight patients with advanced and metastatic endometrial cancer (FIGO stage III-IV; Mutch. Gynecol Oncol. 2009, 115:325-328) were included to the study. All patients were not amenable for treatment for surgery, chemo- or radiotherapy. Tumor tissue samples from the patients were assessed for PR level. Primary progesterone receptor-negative (PR−) cancer was registered in 3 patients; secondary progesterone receptor-negative (PR−) cancer was registered in 5 patients. All patients were treated with oral PR agonist medroxyprogesterone acetate (MPA) at dose of 500 mg once a day and sodium cridanimod (SC) intramuscular injections at dose of 500 mg twice a week. The responses (complete response, partial response or stable disease) according to RECIST 1.0 (www.recist.com; Therasse et al., J. Natl. Cancer Inst., 2000, 92(3):205-216) criteria as well and progression free period were estimated during the study for all patients. The interim results of the trial are shown in Table 1, below.

TABLE 1

| Patient ID [initials] | Status of PR receptor negativity | PR level before adding SC to MPA therapy, fmol/mg of protein | PR level before adding SC to MPA therapy, positive or negative, by IHC | Response at least within the next CT | Duration of SC + MPA untill progression or last evaluation, days |
|---|---|---|---|---|---|
| NLG | Secondary | 2 | Negative | No | NA |
| AAA | Secondary | 0 | Negative | Yes (SD) | 136 |
| ZTA | Secondary | 9 | Negative | Yes (PR) | 84 |
| PLI | Secondary | 0 | Negative | No | NA |
| VNF | Secondary | 8 | Negative | No | NA |
| SME | Primary | 3 | Negative | Yes (SD) | 352 |
| PTV | Primary | 1 | Negative | Yes (SD) | 1414 |
| STP | Primary | 6 | Negative | Yes (SD) | 239 |

In patients with secondary progesterone receptor-negative (PR−) cancer, only two out of five patients showed clinical response (one partial remission and one stable disease lasting for 84 and 136 days, respectively). In contrast, all three patients with primary progesterone receptor-negative (PR−) cancer demonstrated a pronounced clinical response lasting between 239 and 1414 days.

Example 2. A Combination of PR-Agonist and Sodium Cridanimod has Significant Antitumor Effect in an Animal Model of Human Primary PR-Negative Endometrial Cancer and Limited Efficacy in an Animal Model of Human Secondary PR-Negative Endometrial Cancer In order to confirm the above clinical findings, cridanimod/PR-agonist therapy was tested in animal models of human primary and secondary PR-negative cancers:

Mouse Model of Primary PR-Negative Endometrial Cancer:

40 female 8-week-old immunodeficient BNX nu/nu mice (Harlan Laboratories) were bilaterally s.c. injected with $5 \times 10^6$ of human primary PR-negative endometrial cancer cells HEC-1B in 0.1 ml of Matrigel forming two tumors per mouse. Treatment was started on the next day after the injection and discontinued after 5 weeks. Cohorts (10 mice/group) received either:
1) Vehicle control group: vehicle only, 0.9% sodium chloride for injection i.m each alternate day and i.p. for 5 days/week.
2) MA only control group: megestrol acetate (MA) (10 mg/day) i.p. for 5 days/week.
3) SC only control group: sodium cridanimod (SC) (0.3 mg/kg) i.m. each alternate day
4) Combination group (MA+SC): megestrol acetate (MA) (10 mg/day) i.p. for 5 days/week and sodium cridanimod (SC) (0.3 mg/kg) i.m. each alternate day.

Tumors were measured every week with vernier calipers. Tumor size was calculated using the formula: A (length)×B (width)×C (height)×0.5236. The mean±SD of 20 tumors in each animal cohort is shown in Table 2, below.

TABLE 2

| Week/Cohort | 1 (Vehicle) | 2 (MA) | 3 (SC) | 4 (MA + SC) |
|---|---|---|---|---|
| | Tumor volume, mm³ | | | |
| Week 1 | 66 ± 12 | 58 ± 16 | 77 ± 9 | 52 ± 10 |
| Week 2 | 186 ± 26 | 177 ± 19 | 187 ± 22 | 178 ± 15 |
| Week 3 | 412 ± 72 | 510 ± 66 | 488 ± 84 | 212 ± 90* |
| Week 4 | 824 ± 122 | 794 ± 111 | 750 ± 96 | 321 ± 110* |
| Week 5 | 1412 ± 162 | 1383 ± 151 | 1328 ± 135 | 536 ± 159* |

*Statistically significant difference (P less than 0.05) vs cohort 1, 2, and 3, correspondingly.

As shown in Table 2, tumor volumes were significantly different between the experimental (MA+SC combination treatment) and control groups starting at week 3 (P less than 0.05). Thus, a combination of a PR agonist and sodium cridanimod has a significantly enhanced antitumor effect against human primary PR-negative endometrial cancer.

Model of Secondary PR-Negative Endometrial Cancer:

To obtain the secondary progestin-resistant subclones of human endometrial cancer cells, initially progestin sensitive PR-positive effect parent Ishikawa cells were routinely cultured in DMEM/F12 medium supplemented with 5% fetal bovine serum and medroxyprogesterone acetate (MPA) with 2.5 µM increases in MPA concentration (1.0-10 µM) every 4 weeks at 37° C. in a humidified atmosphere of 5% CO2. When the surviving cells had grown to a high density but were still less than confluent, cells were subcloned using 0.02% EDTA and 0.25% trypsin prepared in Hanks' balanced salt solution. MPA-containing medium was replaced every 2-3 days. Cells proliferating in 10 µM MPA with the same doubling time as the initial Ishikawa cells proliferating in the medium without MPA, were considered as secondary progestin-resistant Ishikawa cells. The PR level of the cells was measured by LBA and was 2 fmol per mg of protein and obtained cells were classified as PR– negative.

$2 \times 10^6$ secondary PR negative Ishikawa cells were inoculated into the flanks of MF-1 female nude mice in 100 µl Matrigel. Once tumors had reached approximately 100 mm³ (day "0"), the animals were randomly assigned into four groups of six mice and treated with either:
1) Vehicle control group: vehicle only, –0.9% sodium chloride for injection i.m each alternate day and i.p. for 5 days per week.
2) MPA only control group: medroxyprogesterone acetate (MPA) (250 mg/kg/day) i.p. for 5 days per week.
3) SC only control group: sodium cridanimod (SC) (0.3 mg/kg) i.m. each alternate day
4) Combination group (MPA+SC): MPA 250 mg/kg/day i.p. for 5 days per week and SC 0.3 mg/kg i.m. each alternate day.

Tumors were measured with vernier calipers weekly. Tumor volumes (mm³) were calculated using the modified ellipsoid formula: (length (mm)×width (mm)²)/2. The ratio (percentage) of "Tumor volume at day n" to "tumor volume at day "0" was calculated for each animal. At the end of the experiments (day 35) animals were euthanized. The results for these treatments are shown in Table 3, below.

TABLE 3

| Day #/ Group | 1 (Vehicle) | 2 (MPA) | 3 (SC) | 4 (MPA + SC) |
|---|---|---|---|---|
| | Tumor volume at day n/tumor volume at day "0", %, mean ± SEM | | | |
| 7 | 158 ± 18 | 170 ± 19 | 189 ± 22 | 177 ± 24 |
| 14 | 366 ± 42 | 412 ± 36 | 387 ± 28 | 348 ± 36 |
| 21 | 489 ± 79 | 512 ± 66 | 418 ± 54 | 321 ± 42 |
| 28 | 798 ± 99 | 822 ± 89 | 850 ± 68 | 736 ± 56 |
| 35 | 1112 ± 118 | 1224 ± 99 | 1122 ± 101 | 899 ± 88 |

As shown in Table 3, tumors in the vehicle control-treated group increased in size by 1112±118% after 35 days compared with day "0", the start of the treatment. The group which received a combination of MPA and SC (MPA+SC) showed no statistically significant difference with the corresponding controls. Thus, a combination of a PR agonist and sodium cridanimod has no statistically significant antitumor effect against human secondary PR-negative endometrial cancer.

The above animal data confirm our clinical findings that a combination of a PR agonist and sodium cridanimod has significant antitumor effect in primary PR-negative endometrial cancer and limited efficacy in secondary PR-negative endometrial cancer.

Example 3. A Combination of Tamoxifen and Sodium Cridanimod is Highly Effective for Treatment of Primary ER-Negative Breast Cancer Nine women (48-69 years old) with primary PR/ER– negative (diagnosed using LBA and ICH methods) and HER2 negative (as determined with IHC Dako DakoCytomation's HercepTest), i.e., triple negative breast cancer (TNBC) of stage III-IV not amenable for surgery, chemo- or radiotherapy were treated with tamoxifen (40 mg/day orally) in combination with sodium cridanimod solution injected intramuscularly (i.m.) twice a week at a dose of 500 mg during the first four weeks. After discontinuation of sodium cridanimod, patients continued to take tamoxifen only. The response was assessed each 8 weeks according to RECIST 1.0 criteria (www.recist.com; Therasse et al., J. Natl. Cancer Inst., 2000, 92(3):205-216). The interim results of the trial are shown in Table 4, below.

TABLE 4

| Patient # | PR/ER status | Tamoxifen daily dose, mg | Clinical effect | Progression-free period, months |
|---|---|---|---|---|
| 1 | Negative | 20 | PR | 8 |
| 2 | Negative | 30 | PR | 2 |
| 3 | Negative | 40 | SD | 2 |
| 4 | Negative | 20 | PR | 8 |
| 5 | Negative | 40 | PR | 6 |
| 6 | Negative | 20 | SD | 10 |
| 7 | Negative | 20 | PR | 8 |
| 8 | Negative | 30 | PR | 4 |
| 9 | Negative | 40 | PR | 4 |

As demonstrated in Table 4, seven out of nine women showed partial response lasting between 2 and 8 month, and stable disease was registered in 2 cases. These data provide a foundation for using a combination of cridanimod with a selective ER modulator such as tamoxifen as a therapeutic modality for TNBC stage III-IV patients currently considered incurable.

Example 4. A Combination of Anti-Estrogen Tamoxifen and Sodium Cridanimod has Significant Antitumor Effect in an Animal Model of Human Primary ER-Negative Breast Cancer The MDA-MB-468 (ATCC collection number ATCC® HTB-132, Neve et al., Cancer Cell 2006, 10:515-527) tumor cells (the xenograft of human primary ER-negative breast cancer) were maintained in vitro as a monolayer culture in L-15 medium supplemented with 10% heat inactivated fetal bovine serum, 100 U/ml penicillin and 100 µg/ml streptomycin, and L-glutamine (2 mM) at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

BALB/c nude (Shanghai Sino-British SIPPR/BK Laboratory Animal Co., Ltd.), 6-8 weeks old female mice were inoculated subcutaneously at the right flank with MDA-MB-468 tumor cells ($1\times10^7$) in 0.2 ml of PBS supplemented with BD Matrigel (1:1) for tumor development. The treatments were started on day 17 after tumor inoculation when the average tumor size reached approximately 170 $mm^3$. Tamoxifen, (as citrate salt, of TAM) was given by oral gavage every day in 0.5% methylcellulose water solution; cridanimod (as sodium salt, SC) was injected twice a week (Monday and Thursday) intramuscularly in citrate buffer with pH 8.1. Each group consisted of 8 tumor-bearing mice.

Tumor size was measured twice weekly in two dimensions using a caliper, and the volume was expressed in mm3 using the formula: V=0.5 a×b2 where a and b are the long and short diameters of the tumor, respectively.

Tumor growth inhibition (TGI) was calculated for each group using the formula: TGI (%)=[1−(Ti−T0)/(Vi−V0)]× 100%; Ti is the average tumor volume of a treatment group on a given day, T0 is the average tumor volume of the treatment group on the day of treatment start, Vi is the average tumor volume of the vehicle control group on the same day with Ti, and V0 is the average tumor volume of the vehicle group on the day of treatment start. Significance level was assumed as 0.05. The testing articles administered, doses and tumor growth inhibition data at day 21 in different mice groups are shown Table 5.

TABLE 5

Tumor growth inhibition for cridanimod and tamoxifen in the MDA-MB-468 model of human ER negative breast cancer at day 21

| Treatment | Tumor Volume ($mm^3$) | TGI (%) | p value (vs vechicle control) |
|---|---|---|---|
| Vehicle control (0.9% NaCl) | 355 ± 32 | — | — |
| SC Control (6 mg/mouse) | 209 ± 28 | 78 | 0.024 |
| TAM Control (50 mg/kg) | 473 ± 59 | −65 | 0.094 |
| TAM Control (100 mg/kg) | 355 ± 25 | −1 | 1.000 |
| SC (6 mg/mouse) + TAM (50 mg/kg) | 175 ± 40 | 97 | 0.005 |
| SC (6 mg/mouse) + TAM (100 mg/kg) | 126 ± 28 | 125 | 0.000 |

As shown in Table 5, tumor volumes were significantly different between the experimental (SC+TAM combination treatment) and control groups. Thus, a combination of a anti-estrogen and sodium cridanimod has a significantly enhanced antitumor effect against human primary ER-negative breast cancer.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified is within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treatment of a primary estrogen receptor-negative (ER−) breast cancer in a subject in need thereof, the method comprising the step of administering to the subject (i) an effective amount of cridanimod or a salt or an ester thereof, wherein the effective amount is sufficient to sensitize cancer cells of the subject to inhibitory action of tamoxifen, and (ii) a therapeutically effective amount of tamoxifen.

2. The method of claim 1, wherein the breast cancer is a triple-negative breast cancer.

3. The method of claim 1, wherein the effective amount of the cridanimod or salt or ester thereof is sufficient to induce estrogen receptor (ER) expression in cancer cells of the subject.

4. The method of claim 3, wherein the effective amount of the cridanimod or salt or ester thereof induces ER expression in cancer cells of the subject to the level of more than 10 fmol ER receptors per mg of cytosol protein or until the equal or more than 1% of cancer cells become ER positive as determined by immunohistochemistry staining.

5. The method of claim 1, wherein the method of treatment results in complete response (CR) or partial response (CR/PR) or stable disease (SD) as per RECIST criteria.

6. The method of claim 1, wherein the effective amount of the cridanimod or salt or ester thereof is within the range of 1-50 mg/kg/day.

7. The method of claim 1, wherein the cridanimod or salt or ester thereof is administered in a single daily dose, or on each alternate day, or twice a week.

8. The method of claim 1, wherein the cridanimod or salt or ester thereof and the tamoxifen are administered concurrently.

9. The method of claim 8, wherein the cridanimod or salt or ester thereof and the tamoxifen are administered in one composition.

10. The method of claim 8, wherein the cridanimod or salt or ester thereof and the tamoxifen are administered in two separate compositions.

11. The method of claim 1, wherein the cridanimod or salt or ester thereof is administered prior to the tamoxifen.

12. The method of claim 3, wherein, prior to the administration of the cridanimod or salt or ester thereof and the tamoxifen, the expression level of ER is determined in a cancer sample obtained from the subject.

13. The method of claim 12, wherein the expression level of ER is determined using a ligand binding assay.

* * * * *